(12) United States Patent
Faul et al.

(10) Patent No.: US 6,608,688 B1
(45) Date of Patent: Aug. 19, 2003

(54) WIRELESS OPTICAL INSTRUMENT FOR POSITION MEASUREMENT AND METHOD OF USE THEREFOR

(75) Inventors: Ivan Faul, Boulder, CO (US); Waldean A. Schulz, Boulder, CO (US); Brett R. Skelton, Boulder, CO (US); Ronald M. Pasquini, Boulder, CO (US)

(73) Assignee: Image Guided Technologies, Inc.

( * ) Notice: Subject to any disclaimer, the term of this patent is extended or adjusted under 35 U.S.C. 154(b) by 0 days.

(21) Appl. No.: 09/647,365

(22) PCT Filed: Apr. 2, 1999

(86) PCT No.: PCT/US99/07317

§ 371 (c)(1),
(2), (4) Date: May 16, 2001

(87) PCT Pub. No.: WO99/52094

PCT Pub. Date: Oct. 14, 1999

Related U.S. Application Data

(60) Provisional application No. 60/080,587, filed on Apr. 3, 1998, and provisional application No. 60/082,945, filed on Apr. 24, 1998.

(51) Int. Cl.⁷ .............................................. G01B 11/14
(52) U.S. Cl. ..................................................... 356/614
(58) Field of Search ..................... 356/614, 3; 250/221; 345/158, 175, 176, 179, 180, 182, 166

(56) References Cited

U.S. PATENT DOCUMENTS

| | | | | |
|---|---|---|---|---|
| 4,396,945 A | * | 8/1983 | DiMatteo et al. | 348/139 |
| 4,565,999 A | * | 1/1986 | King et al. | 340/825.19 |
| 4,578,674 A | * | 3/1986 | Baker et al. | 345/159 |
| 4,895,440 A | * | 1/1990 | Cain et al. | 172/4.5 |
| 5,440,112 A | * | 8/1995 | Sakimura et al. | 250/203.1 |
| 5,572,317 A | * | 11/1996 | Parker et al. | 250/203.3 |
| 5,574,479 A | * | 11/1996 | Odell | 345/158 |
| 5,608,528 A | * | 3/1997 | Ogawa | 356/620 |
| 5,771,978 A | * | 6/1998 | Davidson et al. | 172/2 |
| 5,819,206 A | | 10/1998 | Horton et al. | |
| 5,831,601 A | | 11/1998 | Vogeley et al. | |
| 5,923,417 A | * | 7/1999 | Leis | 356/141.1 |
| 5,945,981 A | * | 8/1999 | Paull et al. | 345/180 |
| 6,016,455 A | * | 1/2000 | Ohtomo et al. | 356/73 |
| 6,133,998 A | * | 10/2000 | Monz et al. | 356/141.1 |
| 6,181,329 B1 | * | 1/2001 | Stork et al. | 345/179 |

* cited by examiner

*Primary Examiner*—Michael P. Stafira
(74) *Attorney, Agent, or Firm*—McCracken & Frank

(57) ABSTRACT

Disclosed is a wireless instrument tracking system. The wireless instrument tracking system is used for determining the location of at least one point relative to the instrument in a three-dimensional space relative to a three-dimensional coordinate tracking system. Advantageously, a first wireless instrument can be placed into the optical field with the wireless instrument including a wireless receiver and at least one optical position indicator. The optical position indicator is typically light emitting diodes (18) and communicates with corresponding measurement sensors (30) across a wireless optical link. The wireless optical link is time multiplexed with repetitive time frames divided into time slots. Each LED (18) emits an infrared signal or flashes in a respective time slot of a time frame. The measurement sensors (30) are preferably CCD cameras. The LEDs (18) are synchronized with the cameras and once synchronized each LED (18) flashes in a different time slot in synchronization with the camera frame rate.

83 Claims, 2 Drawing Sheets

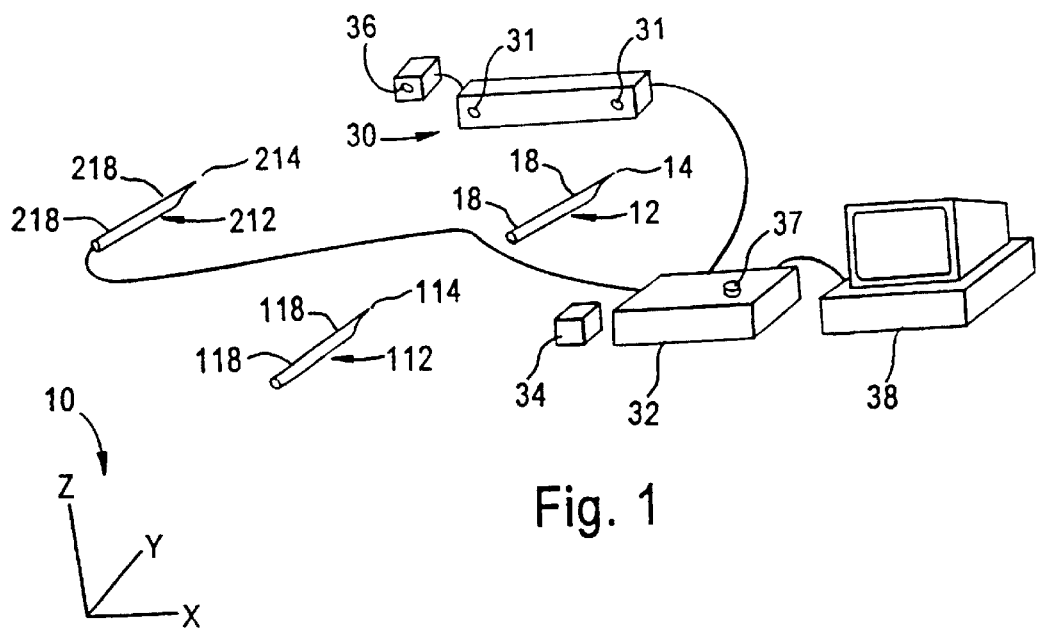
Fig. 1
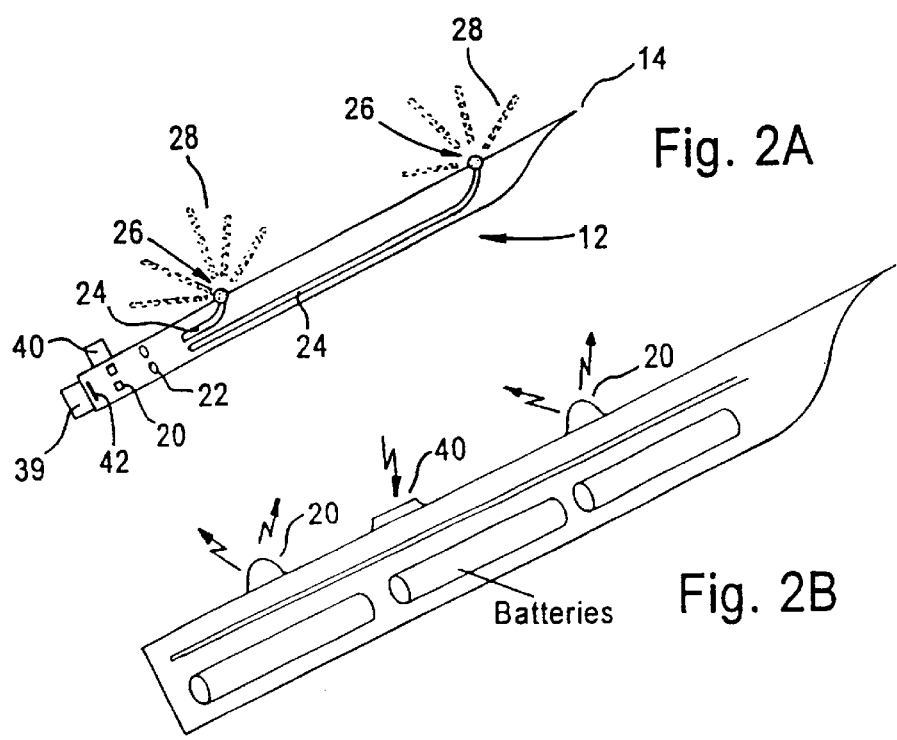
Fig. 2A
Fig. 2B

WIRELESS OPTICAL INSTRUMENT FOR POSITION MEASUREMENT AND METHOD OF USE THEREFOR

This application claims priority of U.S. Provisional Patent Application Ser. No. 60/080,587 filed Apr. 3, 1998, entitled "OPTICALLY TRACKED WIRELESS INSTRUMENTATION" and U.S. Provisional Patent Application Ser. No. 60/082,945 filed Apr. 24, 1998, entitled "WIRELESS MEASUREMENT INSTRUMENT AND SYSTEM FOR POSITION MEASUREMENT AND METHOD OF USE THEREFOR", the disclosures of which are incorporated by reference herein in their entirety.

FIELD OF THE INVENTION

The present invention relates to optical instruments for position measurement, and more particularly, is directed to wireless optical instruments for position measurement.

BACKGROUND OF THE INVENTION

Systems using wired optical instruments for position measurement are known. One such system is an a FlashPoint 5000 system (FP5000) which is commercially available from Image Guided Technologies, Boulder, Colo. The FP5000 system includes multiple instruments, a camera system and a control unit. The control unit sends synchronization signals to the instruments via instrument cables and a break out box (if equipped). A measurement camera system includes two or more camera heads. By receiving the synchronization signals, infrared light emitting diodes (LEDs) on the instruments flash in synchronization with the camera frame rate (individually or in groups, time multiplexed). Each of the cameras images light emitted by the LEDs, and the measurement system uses the images to provide data. The data are converted to measurement angles by the measurement system and the measurement angles are sent to the control unit. The control unit converts the measurement angles to x, y and z coordinates of the LEDs. The control unit can convert the locations of the LEDs to an x, y, z position of the instrument and an orientation of the instrument. The instrument can, in addition, transmit instrument data to the control unit via the instrument cable. This information includes: button states, calibration data, probe ID, type and serial number, probe tip length, temperature and pressure.

Although wired optical instruments are satisfactory in the majority of applications, the requirement for a wire to connect the instrument to the control unit can be cumbersome. Thus, there is a need in the art for a system using a wireless optical instrument for position measurement.

SUMMARY OF THE INVENTION

It is, therefore, an object of the present invention to provide a system using a wireless instrument for position measurement.

Another object of the present invention is to provide an apparatus and method of use thereof in which a wireless optical instrument is synchronized with a controller.

It is yet a further objective of the present invention to provide a method of anticipating when an optical indicator should emit light.

Yet another object of the present invention is to provide a method where additional wireless instruments can be introduced into an optical field and assigned a particular multiplexed time slot.

Yet another object of the present invention is to provide a method of time multiplexing multiple optical instruments in an optical field.

These and other objects of the present invention are achieved by a wireless instrument tracking system. The wireless instrument tracking system is used for determining the location of at least one point in a three dimensional space relative to a three dimensional instrument tracking system. Advantageously, a first wireless instrument can be placed into the optical field with the wireless instrument including a wireless receiver and at least two optical position indicators. Two optical position indicators are required to compute orientation, but if only the location of the instrument is needed, one optical position indicator would suffice. The optical position indicators are typically light emitting diodes (LEDs) and communicate with corresponding position measurement sensors across a wireless optical link. The wireless optical link is time multiplexed with repetitive time frames divided into time slots. Each LED emits an infrared signal or flashes in a respective time slot of a time frame. The measurement sensors are preferably charge coupled device (CCD) cameras. The LEDs are synchronized with the cameras and once synchronized each LED flashes in a different time slot in synchronization with the camera frame rate (individually or in groups). Additional wireless instruments can be placed into the optical field. In a non-auto configuring system, each instruments is preassigned to a particular time slot Because each instrument is pre-assigned a time slot, a carrier signal can be used to trigger the emitters. Advantageously, in an automatically configuring system, additional wireless instruments are not assigned a particular time slot but instead use one time slot as a search channel. The additional instrument is called an unconfigured instrument. The unconfigured instrument or instruments (for example, at startup) are dynamically assigned to a particular time slot by the controller. Collisions are arbitrated using known arbitration schemes such as an ALOHA scheme.

The foregoing objects are also achieved by a wireless instrument tracking system for determining the location of at least one point in three dimensional space relative to a three dimensional instrument tracking system. The instrument tracking system includes a first wireless instrument, including a receiver and at least one optical position indicator. At least two corresponding sensors sense optical signals emitted from the at least two optical position indicators across an optical link. A controller includes a transmitter which can transmit signals to the receiver across a wireless link and means are provided for determining the location of the one optical position indicator relative to the coordinate system.

The foregoing objects are also achieved by a method of determining a location of at least one point in an optical field, the optical field being a three dimensional space relative to a three dimensional coordinate system. A first wireless instrument is placed into the optical field. The first wireless instrument includes a receiver and at least one optical position indicator. The first wireless instrument is synchronized with a controller. The controller includes a transmitter that can transmit signals to the receiver across a wireless link. The optical position indicator may also transmit data and synchronization to receivers associated with the controller, by modulating the output from the position indicators.

The system transmits synchronization signals to the instruments via the wireless link. Upon receiving the synchronization signals, the infrared LEDs on the instruments flash in synchronization with the camera frame rate. The measurement camera array images the LEDs, converts the data to measurement angles and sends it to the control unit. The control unit converts the measurement angles to x, y and z coordinates of the LEDs, and eventually, if required, to an x, y, z position and orientation of a rigid body having multiple LEDs are attached to. The instruments can, in addition, transmit instrument data to the control unit via the wireless link. The data can include button states, calibration data, probe ID, type and serial number, probe tip length, temperature and pressure.

Still other objects and advantages of the present invention will become readily apparent to those of ordinary skill in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein:

FIG. 1 is a perspective schematic view of the wireless system of the present invention;

FIG. 2 is a perspective view of a probe, light source and optical indicators;

BEST MODE CONTEMPLATED FOR CARRYING OUT THE INVENTION

Figure 3:
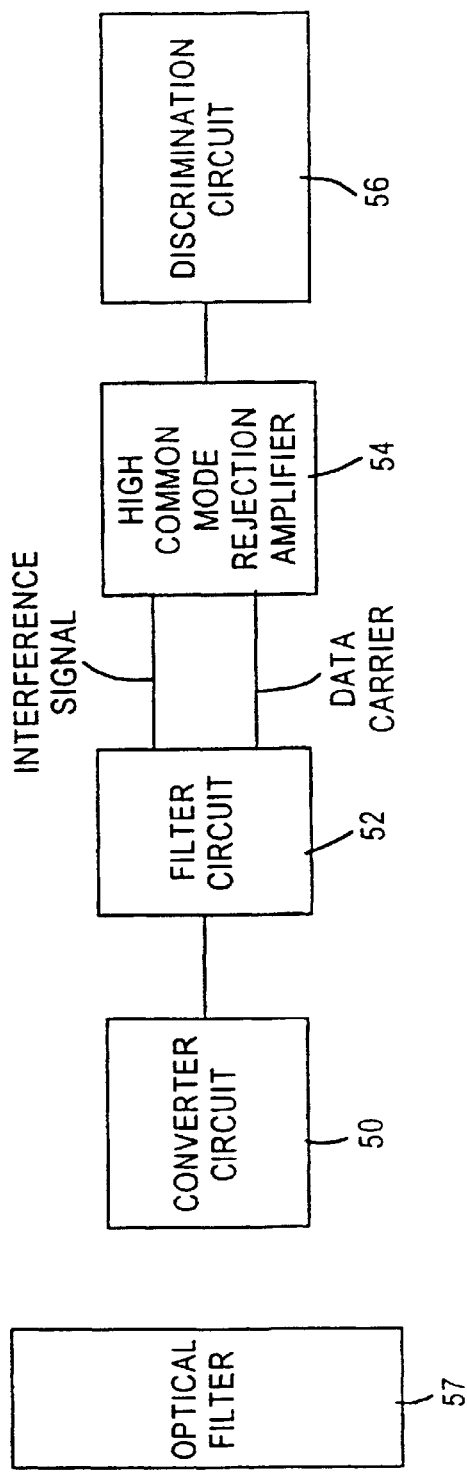
FIG. 3 is a schematic diagram of a converter circuit.

A method and apparatus of using and configuring a wireless instrument in an optical field in accordance with the present invention are described. In the following description, for purposes of explanation, numerous specific details are set forth in order to provide a thorough understanding of the present invention. It should be apparent, however, that the invention may be practiced using other, different specific details. In other instances, well-known structures and devices are shown in block diagram form in order to avoid unnecessarily obscuring the present invention.

In FIG. 1, a rectangular three dimensional coordinate system generally indicated at 10 is illustrated. An optical tracking system for measuring the location and orientation of an optical probe is also depicted in FIG. 1. As used herein, position means the location or orientation (as in an upright or inverted position). Thus, position includes a location and orientation. The system includes a first wireless optical probe, generally indicated at 12, that has a tip 14. The system also includes a second wireless optical probe, generally indicated at 112, that has a tip 114. A wired probe is generally indicated at 212 that has a tip 214. The system can accommodate any number of objects to be simultaneously tracked, although tracking of up to about eight objects is preferred. Each of the probes 12, 112, 212 is considered an object to be tracked. On the object to be tracked, depicted as the probe 12 are located energy emitting elements 18 such as LEDs. The energy emitters include optical position indicators such as LEDs. Alternatively, passive markers such as reflective, shiny balls can be substituted for the energy emitters 18. The energy emitters 18 are preferably electromagnetic ray emitters. Object 12 need not be a probe as depicted, but also can be a reference frame, removable pod, a single LED or any other object to be tracked in the three dimensional coordinate system. The instruments can be identical or different. An exemplary reference frame is a Dynamic Reference Frame™ (DRF), commercially available from Image Guided Technologies, Boulder, Colo.

In FIG. 2, two light emitting diodes 20 are depicted which serve as generators of electromagnetic radiation (the light sources). Although the invention contemplates any number of light sources, only two light sources per probe 12, 112, 212 are depicted. Each energy emitter 20 can disperse the light into a wide radiation pattern 28. Other and different instruments can be used as described in co-pending patent application Ser. No. 08/870,296 filed Jun. 6, 1997, entitled "Optical Fiber Probe for Position Measurement" which is assigned to the instant assignee and which is incorporated into the present specification in its entirety.

A sensor assembly 30 includes at least two charge coupled device cameras 31 as depicted in FIG. 1. Exemplary electromagnetic rays 28 radiate outward from each of the emitter elements, a few of which are seen by each of the CCD cameras 31. A controller 32 controls the sensor assembly 30 and the light sources. A transceiver 34 is coupled to controller 32 as depicted in FIG. 1. A photo diode 36 is coupled to the sensor assembly 30 and is in communication with controller 32. Optionally, a contact or connector 37 is mounted to controller 32 and is used to transfer information to a mating connector or contact 39 mounted on one end of probe 14 as depicted in FIG. 2. An otherwise conventional computer 38 receives input of the data from controller 32. From these data, computer 38 can calculate the x, y, z coordinates of the location of each element, 18 or 26, etc., which appears as a substantial point source of light. From the thus determined coordinates of each emitter, and the known geometry of the probe, the computer 38 can also compute the location and orientation of the probe and therefore can determine the location of any point on the probe, such as the probe tip. Computer 38 also determines the unit 3-D vector describing the longitudinal direction of the probe (which is one aspect of the orientation of the probe). These calculations can also be performed by the controller 32. If more than two non-collinear electromagnetic energy ray emitters are disposed on the probe, a transverse 3-D vector can also be computed to describe the rotational orientation of the probe or its yaw-pitch-and-roll angles.

The light from each LED can be modulated and the modulated light can be received by the photo diode 36. Because the signal is modulated, additional information can be included and sent to the controller 32. Because the cameras 31 integrate the light signal, the cameras do not sense that the light signal is being modulated. The photocells 36 or photodiodes are not used to sense the location of the instruments 12, 112.

Optional connector 37 and connector 39 can be used in addition or alternatively to transfer information from the probe to the control unit or from the controller 32 to the probe 12, 112. A momentary contact at the beginning of the procedure between probe 12, 112 and the controller 32 can be used for the transmission of "smart" information to the controller 32 and to "register" the probe's existence as an active instrument to the controller 32. The transfer of such "smart" information to the controller 32 includes a transfer of information such as instrument calibration, serial number, instrument ID, and the like. The storage and transmission of such information across wires is already covered by U.S. Pat. No. 5,617,857, entitled "Imaging System Having Inner Active Medical Instruments and Method" and is assigned to the instant assignee and is hereby incorporated into the present specification in its entirety.

Mounted on the probe 12 is a wireless transceiver 40, as depicted in FIG. 2. Transceivers 34 and 40 are in wireless communication with each other over a wireless link.

The probe 12 includes a memory module 42 in which is stored the smart information. The memory module 42 may be integrally formed with the probe 12 or included as a separate attachment. The EPROM chip may be preprogrammed with a variety of initialization information including the serial number of the instrument, the instrument type or part number, the number of buttons on the instrument, the number of energy-emitting elements on the instrument, the local x, y, z coordinates of the tip or other reference location on the instrument, the local unit direction vectors of the "longitudinal direction" of the instruments, the local unit direction vectors of the "transverse direction" of the instrument, the local x, y, z coordinates for each of the energy-emitting elements, customer specific information and the like.

In FIG. 3, a circuit is depicted for rejecting interfering light signals when the wireless link uses light energy in the IR range. The circuit includes a circuit converter 50 which converts an incoming light signal received by a sensor 40 into an electrical signal. 30 The converted electrical signal includes both a data carrier as well as an unwanted ambient interference signal. A filter circuit 52 is coupled to the converter circuit 50. The filter circuit 52 separates the interference signal from the combined signal relying on the fact that the interference signal is of a much lower frequency. An interference signal and data carrier signal are output from filter circuit 52 separately presented to a high common mode rejection amplifier 54 which provides more amplification to the data carrier signal than to the interference signal. A discrimination circuit 56 is coupled to the amplifier 54 and can discriminate between the data carrier frequency that is known and any interference signal that may remain in the output of the data carrier signal.

Additional buttons can optionally be provided on the probe 12. This would provide for "wireless" buttons, either on the instrument or provided separately. A separate button would require an additional emitter 18 for transmission of its state.

Optical filters 57 can be used to block unwanted ambient light energy. These filters can be short pass or long pass or a combination of both to provide a band pass function.

Advantageously, the present invention is able to operate under high ambient lighting conditions such as operating room (OR) lights (medical applications) or sunlight (industrial applications). This is accomplished by a combination of filtering, common mode rejection and frequency discrimination as depicted in FIG. 3.

There are two wireless data communication links used in the present invention. The first data link is a wireless data link between transmitter 34 and receiver 40 mounted on probe 14. This data communication link can be infrared, radio frequency or ultra sound. The second wireless communication link is between emitters 18 or 26 and receiver 36.

Figure 4:
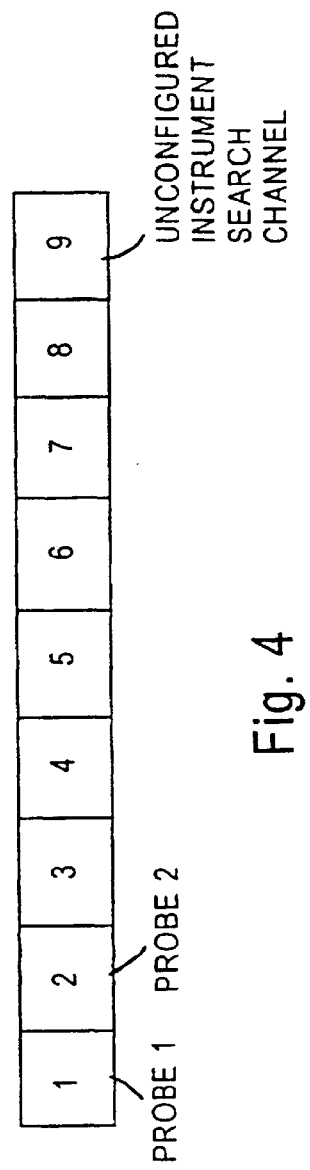
FIG. 4 is an illustration of time slots within a time frame.

Both of the wireless links are divided into time frames, that is, each is time multiplexed. For example, as depicted in FIG. 4, a time frame could be divided into nine time slots, the duration of which depends on the number of markers or emitters on the instrument. In this configuration, eight wireless instruments can be placed into the optical field with each having a time slot associated therewith. Each instrument would be assigned the same time slot for the wireless link as well as for the optical link with a possible slight time off set between the time slots. The ninth time slot will serve as a search channel for adding unconfigured instruments to the system. The optical time slot might be slightly delayed behind the wireless time slot. In accordance with the present invention, a wireless instrument needs to be synchronized to the controller 32 so that the optical indicators 18 or 26 will emit light or flash in synchronization with the camera frame rate. One way of maintaining synchronization between the wireless probe and controller 32 is to use a high accuracy, low drift clock in both the control unit and wireless instrument 12 which would require only initial or infrequent synchronization between controller 32 and probe 12.

The system could also derive synchronization from a common external source, such as the 60 or 50 hertz that is being radiated by nearby electrical apparatus. The system could also derive synchronization from time signals being transmitted by satellites, other wireless carriers or infrared strobes.

One advantage of using a low drift clock is that a problem occurs if an instrument loses line-of-sight contact with the controlling synchronization signal and that the LED timing cannot be extracted. Utilizing low drift, high accuracy clocks in both probe 12 and controller 32 allows both to run without any signaling therebetween for a significant time period after initial synchronization. The length of the time period is determined by the stability of the clocks. The clock stability can be chosen to maintain synchronization and to only bridge temporary communication drop outs, or it can be chosen to ensure synchronization during the entire use of the wireless instrument 12. In the latter case, the instrument 12 that was synchronized with the controller 32 at the beginning of a measurement session would not have to be resynchronized during the same session.

Another method which would reduce system complexity by not requiring data communication to the wireless instruments, would be achieved by having the wireless instrument 12 fire its indicators or LEDs 18 asynchronously of their own accord. The controller 32 would learn the asynchronous firing pattern and would synchronize its measurement functions by using the timing information derived from the wireless instrument 12.

Yet another method of facilitating synchronization of the controller 32 and all instruments 12, 112 would be to use an external clock that would establish reception of a common clock signal by all instruments 12, 112. This clock signal can be transmitted by a central clock, or can be received from new satellites or already existing satellites (such as GPS satellites) or can be received from radio frequency time beacons.

Unlike a conventional wired system in which the controller 32 can discern the addition of an additional probe 12, in a wireless system the controller 32 must be able to recognize that an additional instrument 12 has entered the optical field. Two systems are possible: a first and simpler system termed a non-auto configure system, and a second system termed an auto configuring system. The advantage of the auto configuring system is that instruments do not have to be pre-assigned to a particular time slot.

In a non-auto configuring system, each instrument 12, 112, 212 would be assigned or dedicated to a particular time slot. The position indicators 18 of each instrument can be synchronized in a non-auto configuring system in one of two ways. In the first way, the transmission of the carrier only indicates the time slots for emitters 18 to emit energy such as LED flashes. The presence of a carrier will signal to the instrument 12, 112, that an LED should be fired. In the absence of the carrier, no LEDs will be fired. The carrier pulses are counted by each of the wireless instruments 12, 112, and the next LED is fired after each consecutive pulse is counted. Each instrument is assigned a number of LEDs in the pulse sequence. For instance, 20 pulses are transmitted to five probes, each containing four LEDs. Instrument 1 will fire its LEDs during the first four carrier pulses (pulses 1 through 4), instrument 2 during the second four pulses pulses 5 through 8) until instrument 5 fires its LEDs during the last four pulses (pulses 17 through 20). At the end of the cycle, instrument 1 will again pick out pulses 1 through 4. This method of time multiplexing will distinguish one instrument 12, 112 from another instrument 12, 112. To synchronize the instruments with the start of the carrier pulse stream, a "quiet" time during which no pulses are transmitted precedes the pulse stream in order to synchronize the instruments.

A slightly more complex but more intelligent method of controlling instrument energy emitters 18 or LEDs is the transmission of an instrument identification code (ID) as an "address" indicating which instrument 12 should fire its LEDs. The transmission of synchronization pulses to the instruments 12, 112 would be similar to the previously described method, except that the pulse does not include only a carrier, but also includes a modulated signal. The modulated signal contains data representative of an LED identifier. The LED identifier is received by all instruments and if it matches the ID of an LED on a specific instrument, that instrument will fire that particular LED. The LED identifier can be transmitted multiple times during a pulse to improve immunity against noise and false reception. In the implementation of the system for use under noisy conditions, the number of ID transmissions per pulse is unique to the instrument and each ID is counted. The instrument 12, 112 can thus anticipate the end of the pulse transmission and if a drop out occurs, it will self-time the pulse duration and turn the LED off at the correct time.

The auto configuring network allows instruments to be introduced into the optical field and removed from the optical field. Unconfigured instruments will be automatically recognized when first introduced into the optical field, uncommitted time slots will be arbitrated, and the instrument will be added to the active list of instruments being tracked. Collisions due to the simultaneous introduction of multiple increments will be resolved.

The operation of the auto configuration method is as follows. During operation with multiple instruments visible in the field, each instrument operates in a time slot assigned to that instrument after first being introduced into the optical field. Each optical instrument, however, is not pre-assigned to a particular time slot. Thus, more than eight instruments can be used within the system although only eight can be tracked at any particular time. Within an allotted time slot, the instrument sequentially fires all the LEDs it contains. When a new instrument is introduced into the optical field, it does not have a time slot assigned and cannot fire its LEDs without potentially interfering with existing instruments 12, 112 already in the optical field. The new instrument is referred to as an unconfigured instrument and the existing active instruments are referred to as configured instruments.

A method is established where all unconfigured instruments are assigned a shared time slot (search channel) that is used whenever the unconfigured instrument is brought into the field of view for the first time. An unconfigured instrument communicates with the controller 32 in this time slot until it is assigned to a dedicated time slot. This instrument then becomes a configured instrument. If multiple instruments are brought into the field of view simultaneously, data collisions can occur as more than one instrument attempts to communicate with the controller 32 at the same time. A data arbitration scheme is implemented to resolve such conflicts. This will happen, for example, if multiple instruments are in the field of view when the system first starts operation. To facilitate the unique identification of each instrument and the LEDs it contains, an LED identification code will be transmitted by the controller 32. One method of resolving such collisions is known as the ALOHA method which is well known in the art.

For either the auto configuring or the non-auto configuring systems, where the wireless link is bit rate limited (such as RF and ultrasound), a protocol that enables the instrument 12, 112 to "anticipate" the next LED to flash by providing advance information will be possible. A predictive algorithm operates as follows: a control circuit in the controller 32 records the sequence of LEDs that are being flashed. The sequence is analyzed to determine the repetitive pattern's length and the specific sequence of LEDs in the pattern. By having learned the LEDs sequence, the control circuit of the controller 32 knows ahead of time when an LED will be asked to turn on during the ongoing cycling through the LED sequence. This "prediction" will be transmitted to the wireless transducer at least one LED time slot ahead of the actual turning on of each LED. This will allow the complete transmission of which LED is required to turn on before it is necessary to actually turn it on, facilitating the timely turn-on of the LED. This is particularly useful for ultrasound which also involves additional propagation delays, which in fact would force the controller 32 to estimate the extra propagation time based on the last known location of the instrument 12, 112.

It should now be apparent that a system for using a wireless instrument has been described in which the wireless instrument or instruments can be synchronized to a controller. Advantageously, up to eight wireless instruments can be introduced into the field of view at any one time. In a non-auto configuring network, the system is limited to using eight instruments which are pre-assigned to particular time slots. In an auto configuring network, more than eight instruments can be used of which only eight instruments being used at any one time.

It will be readily seen by one of ordinary skill in the art that the present invention fulfills all of the objects set forth above. After reading the foregoing specification, one of ordinary skill will be able to affect various changes, substitutions of equivalents and various other aspects of the invention as broadly disclosed herein. It is therefore intended that the protection granted hereon be limited only by the definition contained in the appended claims and equivalents thereof.

What is claimed is:

1. A tracking system for tracking the location of an object in three dimensional space, the system comprising:
   the object having a wireless receiver and first and second optical position indicators;
   controlling apparatus in communication with the receiver and operable therewith to direct the indicators to provide signals; and
   a detector capable of detecting the signals so that the system can determine the location of the object.

2. The system of claim 1, wherein the receiver is a transceiver.

3. The system of claim 1, wherein the optical position indicators emit electromagnetic radiation.

4. The system of claim 3, wherein the optical position indicators are LED's.

5. The system of claim 1, wherein the optical position indicators are reflective markers.

6. The system of claim 4, further comprising a converter.

7. The system of claim 3, further comprising modulation sensors for sensing a modulated optical signal emitted from each of the optical position indicators.

8. The system of claim 7, wherein the modulation sensor comprises a photodiode.

9. The system of claim 1, wherein the detector includes first and second CCD cameras.

10. The system of claim 9, further comprising a third optical position indicator, non-collinear with the other optical position indicators, wherein the indicators enable determination of pitch, roll, and yaw data of the object.

11. The system of claim 1, wherein the controlling apparatus includes a transmitter.

12. The system of claim 1, wherein the object includes a memory.

13. The system of claim 12, further comprising means for transferring information from said memory to said controller.

14. The system of claim 1, wherein communication between the controlling apparatus and the receiver is through one of an infrared link, a radio frequency link, or an ultrasound link.

15. The system of claim 1, wherein communication between the detector and the signals comprises an optical link divided into repetitive time frames, each time frame divided into repetitive time slots.

16. The system of claim 15, wherein the object comprises a first object and the wireless receiver comprises a first wireless receiver, the system further comprising a second object having both a second wireless receiver and two optical position indicators.

17. The system of claim 16, wherein the first object is assigned a particular time slot in each time frame and the second object is assigned a particular different time slot in each time frame.

18. The system of claim 12, wherein the duration of each time frame is dependent on the number of optical position indicators mounted on each object.

19. The system of claim 1, wherein the signals and the controlling apparatus are time multiplexed.

20. The system of claim 19, wherein the receiver and the controller each further comprise a low drift clock allowing the receiver and controller to maintain prolonged synchronization with respect to each other.

21. The system of claim 19, wherein the receiver and the controller are synchronized from an external source.

22. The system of claim 21, wherein the external source is a time signal received from one of a satellite, a radio frequency time beacon, or radiation of surrounding electrical apparatus.

23. The system of claim 1, wherein the object is one of a probe, a reference frame, a removable pod, or a single LED.

24. The system of claim 1, further comprising an optical filter.

25. The system of claim 24, wherein the optical filter comprises a combination of short and long pass optical filters.

26. The system of claim 1, further comprising a filter circuit.

27. The system of claim 26, further comprising an amplifier.

28. The system of claim 27, further comprising a discrimination circuit.

29. The system of claim 1, further comprising a button disposed on the object for transmitting state information.

30. The system of claim 1, further comprising a wired instrument connected to the controlling and processing apparatus by a wired path.

31. A tracking system for tracking the location of an object in three dimensional space, the system comprising:
the object having first and second optical position indicators that fire signals autonomously in a timed pattern;
a detector capable of detecting the pattern; and
controlling apparatus capable of learning the pattern and synchronizing measurements with the timed pattern.

32. The system of claim 31, wherein the optical position indicators emit electromagnetic radiation.

33. The system of claim 32, wherein the optical position indicators are LED's.

34. The system of claim 33, wherein the detector includes first and second CCD cameras.

35. The system of claim 34, further comprising a third optical position indicator, non-collinear with the other optical position indicators, wherein the indicators enable determination of pitch, roll, and yaw data of the object.

36. The system of claim 35, wherein the object includes a memory.

37. The system of claim 36, wherein communication between the detector and the signals comprises an optical link divided into repetitive time frames, each time frame divided into repetitive time slots.

38. The system of claim 37, wherein the object is a first object assigned a particular time slot in each time frame, the system further comprising a second object capable of being assigned a particular different time slot in each time frame.

39. A tracking system for tracking the location of a plurality of objects in three dimensional space, the system comprising:
each of the objects having a wireless receiver and first and second optical position indicators that provide a position signal for each object;
controlling apparatus that transmits synchronization pulses to cause each of the objects to provide a position signal at a designated time slot; and
a detector capable of detecting the signals so that the system can determine the location of each of the objects.

40. The system of claim 39, wherein the receiver is a transceiver.

41. The system of claim 39, wherein the optical position indicators are LED's.

42. The system of claim 41, wherein the receiver and the controller each further comprise a low drift clock allowing the receiver and controller to maintain prolonged synchronization with respect to each other.

43. The system of claim 41, wherein the receiver and the controller are synchronized from an external source.

44. The system of claim 41, further comprising a third optical position indicator, non-collinear with the other optical position indicators, wherein the indicators enable determination of pitch, roll, and yaw data of the object.

45. A tracking system for tracking the location of a plurality of objects in three dimensional space, the system comprising:
each of the objects having a wireless transceiver and first and second optical position indicators that provide a position signal for each object;

a detector capable of detecting the signals so that the system can determine the location of the object; and controlling apparatus incorporating a search channel time slot and a plurality of other time slots wherein the controlling apparatus is capable of recognizing objects during the search slot and wherein the controlling apparatus is also capable of assigning each of the objects to one of the other time slots.

46. The system of claim 45, wherein the optical position indicators are LED's.

47. The system of claim 45, further comprising a third optical position indicator, non-collinear with the other optical position indicators, wherein the indicators enable determination of pitch, roll, and yaw data of the object.

48. The system of claim 47, wherein the objects each include a memory.

49. The system of claim 48, further comprising means for transferring information from each memory to the controller.

50. A method of tracking the location of an object in three dimensional space, the method comprising the steps of:

providing the object a wireless receiver and disposing first and second optical position indicators in fixed relation to the object;

controlling the indicators to provide signals through communication with the receiver; and detecting the signals with a detector so that the system can determine the location of the object.

51. The method of claim 50, wherein the receiver is a transceiver.

52. The method of claim 50, further comprising the step of transferring data from the object to controlling apparatus.

53. The method of claim 52, wherein the data is one of a serial number for the object, calibration data of the object, or identification data of the object.

54. The method of claim 50, wherein the optical position indicators are LED's.

55. The method of claim 50, further comprising the step of disposing a third optical position indicator on the object, non-collinear with the other optical position indicators, wherein the indicators enable determination of pitch, roll, and yaw data of the object.

56. The method of claim 50, wherein the object includes a memory.

57. The method of claim 50, wherein controlling the indicators is accomplished by one of an infrared link between controlling apparatus and the object, a radio frequency link between controlling apparatus and the object, or an ultrasound link between controlling apparatus and the object.

58. The method of claim 50, wherein detection of the signals includes establishing an optical link divided into repetitive time frames, each time frame divided into repetitive time slots.

59. The method of claim 58, further comprising the step of providing a plurality of objects each having both a receiver and optical position indicators wherein each of the objects is assigned a particular time slot.

60. The method of claim 59, wherein the optical position indicators of each object emit electromagnetic radiation during the time slot assigned to each respective object.

61. The method of claim 59, wherein one of the repetitive time slots is used as a shared time slot to arbitrate assignment of the objects.

62. The method of claim 61, wherein an ALOHA scheme is used to arbitrate data collisions from multiple objects.

63. The method of claim 50, wherein the object comprises a first object and the wireless receiver comprises a first wireless receiver, the method further comprising the step of providing a second object having both a second wireless receiver and two optical position indicators.

64. The method of claim 50, further comprising the step of providing each of the receiver and the controller a low drift clock allowing the receiver and controller to maintain prolonged synchronization with respect to each other.

65. The method of claim 50, further comprising the step of synchronizing the receiver and the controller with an external source.

66. The method of claim 50, further comprising the step of modulating the signals.

67. The method of claim 50, wherein the object comprises a first object and the receiver comprises a first receiver, the method further comprising the step of providing a second object having a second receiver wherein the second receiver is wired to controlling apparatus.

68. The method of claim 50, further comprising the step of anticipating when the optical position indicators transmit data.

69. The method of claim 68, further comprising the step of recording a sequence of repetitive transmissions of synchronization signals from controlling apparatus and analyzing the sequence to determine the length and pattern of data transmission.

70. The method of claim 50, wherein the controlling step is performed by controlling apparatus that transmits a control signal to the object before the next transmission from the object.

71. The method of claim 50, wherein the detector is in synchronization with the optical position indicators.

72. A method of tracking the location of an object in three dimensional space, the method comprising the steps of:

providing the object with first and second optical position indicators in fixed relation thereto wherein the indicators fire autonomously in a timed pattern;

detecting the signals with a detector; and providing controlling apparatus that learns the pattern and synchronizes measurements with the timed pattern.

73. The method of claim 72, further comprising the step of providing the object a third optical position indicator, non-collinear with the other optical position indicator, wherein the indicators enable determination of pitch, roll, and yaw data of the object.

74. The method of claim 73, wherein communication between the detector and the signals comprises an optical link divided into repetitive time frames, each time frame divided into repetitive time slots.

75. The method of claim 74, wherein the object is a first object assigned a particular time slot in each time frame, the method further comprising the step of providing a second object and assigning thereto a particular different time slot in each time frame.

76. A method of tracking the location of a plurality of objects in three dimensional space, the method comprising the steps of:

providing each of the objects a wireless receiver and first and second optical position indicators that provide a position signal for each object;

transmitting synchronization pulses from controlling apparatus to cause each of the objects to provide a position signal at a designated time slot; and detecting the signals with a detector so that the system can determine the location of the object.

77. The method of claim 76, wherein the receiver is a transceiver.

78. The method of claim 76, further comprising the step of providing each of the receivers and the controller a low drift clock allowing the receiver and controller to maintain prolonged synchronization with respect to each other.

79. The method of claim 76, further comprising the step of synchronizing the receivers and controller with external source.

80. The method of claim 76, further comprising the step of providing each of the objects with a third optical position indicator, non-collinear with the other optical position indicators, wherein the indicators enable determination of pitch, roll, and yaw data of the object.

81. A method of tracking the location of a plurality of objects in three dimensional space, the method comprising the steps of:

providing each of the objects a wireless transceiver and first and second optical position indicators that provide a position signal for each object;

providing controlling apparatus having a search channel time slot and a plurality of other time slots;

providing a detector having an optical field;

recognizing one or more objects during the search channel time slot;

assigning each of the one or more objects to one of the other time slots; and detecting signals from the one or more of the objects so that the system can determine the location of the one or more objects.

82. The method of claim 81, further comprising the step of providing each of the objects a third optical position indicator, non-collinear with the other optical position indicators, wherein the indicators enable determination of pitch, roll, and yaw data of the by object.

83. The method of claim 81, wherein each object is recognized during the search channel time slot upon entering the optical field.

* * * * *